United States Patent
Kim et al.

(10) Patent No.: US 11,096,981 B2
(45) Date of Patent: Aug. 24, 2021

(54) COMPOSITION FOR PREVENTING OR TREATING MUSCLE ATROPHY COMPRISING LYCII RADICIS CORTEX

(71) Applicant: Industry-University Cooperation Foundation Hanyang University Erica Campus, Ansan-si (KR)

(72) Inventors: Chui Young Kim, Anyang-si (KR); Chui Hoon Lee, Seoul (KR); Gyu Sung Jang, Anyang-si (KR)

(73) Assignee: Industry-University Cooperation Foundation Hanyang University Erica Campus, Ansan-si (KR)

(*) Notice: Subject to any disclaimer, the term of this patent is extended or adjusted under 35 U.S.C. 154(b) by 0 days.

(21) Appl. No.: 16/850,344

(22) Filed: Apr. 16, 2020

(65) Prior Publication Data

US 2020/0306333 A1  Oct. 1, 2020

(30) Foreign Application Priority Data

Feb. 21, 2019  (KR) .................. 10-2019-0020348
Jan. 22, 2020  (KR) .................. 10-2020-0008576

(51) Int. Cl.
*A61K 36/815*  (2006.01)
*A23L 33/105*  (2016.01)
*A61P 21/00*  (2006.01)

(52) U.S. Cl.
CPC .......... *A61K 36/815* (2013.01); *A23L 33/105* (2016.08); *A61P 21/00* (2018.01); *A61K 2236/15* (2013.01); *A61K 2236/333* (2013.01)

(58) Field of Classification Search
None
See application file for complete search history.

(56) References Cited

U.S. PATENT DOCUMENTS 10,576,057 B2 * 3/2020 Hwang .............. A23L 2/52
2014/0056863 A1 * 2/2014 Greenberg ........ A61K 31/20
424/93.41

FOREIGN PATENT DOCUMENTS

| KR | 10-0169290 B1 | 12/1998 |
| KR | 10-2006-0112321 A | 11/2006 |
| KR | 10-1083426 B1 | 11/2011 |
| KR | 10-2012-0060002 A | 6/2012 |
| KR | 10-1371194 B1 | 3/2014 |
| KR | 10-1451754 B1 | 10/2014 |

OTHER PUBLICATIONS

Cho, S. et al. An Herbal Formula Consisting of *Schisandra chinensis* (Turcz.) Baill, Lycium chinense Mill and Eucommia ulmoides Oliv Alleviates Disuse Muscle Atrophy in Rats. J of Ethnopharmacology 213:328-339, Mar. 1, 2018. (Year: 2018).*

* cited by examiner

Primary Examiner — Ralph J Gitomer
(74) Attorney, Agent, or Firm — NSIP Law

(57) ABSTRACT

The present disclosure relates to a composition for preventing and treating muscle atrophy, which contains a lycii radicis cortex extract as an active ingredient. The composition of the present disclosure has a remarkable effect of improving muscle atrophy and superior safety and, thus, can be used to prevent and treat muscle atrophy without side effects.

6 Claims, 13 Drawing Sheets

<NF_H&E staing>

COMPOSITION FOR PREVENTING OR TREATING MUSCLE ATROPHY COMPRISING LYCII RADICIS CORTEX

CROSS-REFERENCE TO RELATED APPLICATION

This application claims the benefit under 35 USC 119(a) of Korean Patent Application Nos. 10-2019-0020348 filed on Feb. 21, 2019 and 10-2020-0008576 filed on Jan. 22, 2020, in the Korean Intellectual Property Office, the entire disclosures of which are incorporated herein by reference for all purposes.

TECHNICAL FIELD

The present disclosure relates to a composition for preventing, treating or improving muscle atrophy, etc.

BACKGROUND ART

The skeletal muscle in our body can be largely classified into two types: active muscle (type IIb) consisting of white fast muscle fibers and used to generate motion and postural muscle (type I) consisting of red slow muscle fibers and maintaining posture for a long time with weak force. There also exist type IIa fast muscle fibers having the characteristics of slow muscle fibers.

If muscle mass is decreased due to several reasons, the vicious cycle of degeneration of the musculoskeletal system begins starting from the weakening of muscular power for physical activities. The major symptoms and indications of decreased muscle mass include decreased walking speed, weakened grasping power, etc. and may further lead to injury from a fall, fracture, joint injury, metabolic disorder, cardiovascular diseases, etc. The decreased muscle mass may also be visually perceived with decreased volume of muscle fibers, or muscle atrophy.

The muscle loss (decreased muscle mass) may occur naturally with aging, or may be caused by disuse of muscles, lack of exercise, or other pathological conditions (cachexia, sepsis, starvation, anticancer therapy, or excessive exposure to stress hormones). This can be accounted for by the atrophy of muscle cells due to the anti-anabolic action and catabolic action of the type I and II muscle fibers.

Therefore, as an approach to the muscle atrophy that may be caused by aging, misuse or diseases, naturally derived biological substances that can help maintenance of muscle mass under situations inducing the atrophy of muscle fiber proteins may be used.

In many cases, the stress hormones (cortisol, glucocorticoids, inner GCs) in our body induce molecular biological changes of muscle fibers and are involved anti-anabolic action and catabolic action directly or indirectly. The GCs inhibit the PI3K/Akt/mTOR pathway as an anti-anabolic action, which inhibits downstream effectors such as 4E-BP1, S6K1, etc., thereby preventing the action of eIF4G (eukaryotic translation initiation factor 4 G) and eIF4E (eukaryotic translation initiation factor 4 E). This inhibits mRNA translation for protein synthesis, leading to atrophy of muscle fibers due to inhibited muscle fiber synthesis and protein degradation.

In addition to inhibiting muscle synthesis, the GCs also induce muscle atrophy by degrading proteins. The atrophy-inducing genes, atrogenes (atrogin-1/MAFbx, MuRF-1), are expressed via the mechanism of 'PI3K/Akt→FOXO activation and GSK3 deactivation'. These genes induce protein degradation represented by the ubiquitin-proteasome system.

Lycii radicis cortex refers to the root bark of $Lycium$ $chinense$ Miller or $Lycium$ $barbarum$ L in the family Solanaceae. From old times, the lycii radicis cortex has been used to treat cough, hematemesis, excessive sweating, etc. as an antipyretic or a tonic together with other herbal medicine and to relieve neuralgia, myalgia and joint atrophy.

Prior art 1 (KR 10-1451754, published on Oct. 10, 2014) relates to a composition for preventing metabolic bone disease and improving bone function, which contains an extract mixture of lycii radicis cortex and phlomidis radix. The composition was confirmed to be effective in promoting the proliferation of cells affecting bone metabolism, activating the differentiation of osteoblasts, and having the effect of improving bone density in animal experiments on ovariectomized mice as an osteoporotic animal model. However, this patent is irrelevant of the effect of preventing and improving skeletal muscle atrophy of the present disclosure.

Prior art 2 (KR 10-1371194, published on Sep. 25, 2013) relates to a hypocholesterolemic composition containing a lycii cortex radices (LCR)-derived tyramine derivative and a method for preparing the same. The composition was found to be effective in inhibiting the activity of HMG-CoA reductase and ACAT and reducing total serum cholesterol in animal experiments. In particular, it was found out that the LCR phenolic amide FT has the effect of inhibiting the enzymes at levels comparable to that of FS (feruloylserotonin) derived from safflower seed, and the LCR extract containing the phenolic amide exhibits an excellent effect of lowering serum cholesterol level as compared to serotonin derived from safflower seed even at low concentrations. However, this patent is irrelevant of the effect of preventing and improving skeletal muscle atrophy of the present disclosure.

Prior art 3 (KR 10-2012-0060002, published on Jun. 11, 2012) relates to a composition for preventing and treating dementia or Parkinson's disease, which contains a mori fructus or lycii radicis cortex extract or a mixture thereof as an active ingredient. The mixture was found to have the effect of protecting cells against amyloid-β in the cerebral cortex and the hippocampus, protecting cells against thapsigargin, which is an ER (endoplasmic reticulum) stress toxin, maintaining mitochondrial membrane potential and reducing ROS (reactive oxygen species) production. In addition, it was found to have anti-apoptotic effect by increasing bcl-2, reducing bax and decreasing the activity of caspase-3, neuron-protecting effect via MAP-2 positive cells, and anti-oxidative and anti-apoptotic effects against 6-OHDA (6-hydroxydopamine)-induced toxicity. However, this patent is irrelevant of the effect of preventing and improving skeletal muscle atrophy of the present disclosure.

Prior art 4 (KR 10-1083426, published on Dec. 7, 2010) relates to an anti-diabetic composition containing extracts of lycii radicis cortex, $Cordyceps$ $militaris$ and $Acanthopanax$ $senticosus$. The composition was found to exhibit substantial anti-diabetic effect of inhibiting the activity of α-glucosidase while increasing the activity of glucokinase, pyruvate dehydrogenase and acetyl-CoA carboxylase. However, this patent is irrelevant of the effect of preventing and improving skeletal muscle atrophy of the present disclosure.

Prior art 5 (KR 10-0169290, published on Oct. 9, 1998) relates to a lycii radicis cortex extract and a method for preparing the same. Although the extract preparation process is partly similar to the present disclosure, the purpose and overall preparation method are different.

Prior art 6 (KR 10-2006-0112321, published on Nov. 1, 2006) relates to a preparation for relieving stress and treating depression, which contains lycii radicis cortex and betaine. The extract or composition according to the patent was found to exhibit the effect of enhancing immunity against inflammatory stress and significantly suppressing stress-induced depression as well as improved anti-stress effect. However, this patent is irrelevant of the effect of preventing and improving skeletal muscle atrophy of the present disclosure.

The inventors of the present disclosure have made efforts to find a composition for preventing and treating muscle atrophy. As a result, they have identified that a composition containing a lycii radicis cortex (*Lycium chinense*) extract, and one or more of a $C_1$-$C_4$ lower alcohol and water has superior effect of preventing and treating muscle atrophy (muscle dystrophy), and have completed the present disclosure.

REFERENCES OF RELATED ART

Patent Documents

KR 10-1451754.
KR 10-1371194.
KR 10-2012-0060002.
KR 10-1083426.
KR 10-0169290.
KR 10-2006-0112321.

DISCLOSURE

Technical Problem

The present disclosure is directed to providing a composition for preventing or treating muscle atrophy, which contains a lycii radicis cortex (*Lycium chinense* root or *L. barbarum* root) extract capable of preventing and treating muscle atrophy, as an active ingredient.

The present disclosure is also directed to providing a food composition for preventing or treating muscle atrophy, which contains a lycii radicis cortex extract as an active ingredient.

The present disclosure is also directed to providing a method for preparing the composition for preventing or treating muscle atrophy.

However, the technical problem to be solved by the present disclosure is not limited to the above, and other problems not mentioned above will be clearly understood by those of ordinary skill in the art from the following description.

Technical Solution

The present disclosure provides a pharmaceutical composition for preventing or treating muscle atrophy, which contains a lycii radicis cortex (*Lycium chinense* or *Lycium barbarum*) extract as an active ingredient.

In addition, the present disclosure provides a food composition for preventing or improving muscle loss, which contains a lycii radicis cortex extract as an active ingredient.

In an exemplary embodiment of the present disclosure, the lycii radicis cortex extract may be one extracted with one or more solvent selected from a group consisting of water ($H_2O$), a $C_1$-$C_4$ lower alcohol, n-hexane, ethyl acetate, acetone, butyl acetate, 1,3-butylene glycol, methylene chloride and a mixture thereof, specifically one extracted with a solvent selected from a group consisting of water ($H_2O$), a $C_1$-$C_4$ lower alcohol and a mixture thereof, more specifically one extracted with 50% ethanol.

In another exemplary embodiment of the present disclosure, the composition may decrease the expression of one or more selected from a group consisting of MuRF-1 (muscle RING-finger protein-1) and atrogin-1/MAFbx (muscle atrophy F-box) in myotubes.

In another exemplary embodiment of the present disclosure, the composition may increase the expression of one or more selected from a group consisting of mTOR (mammalian target of rapamycin) and AKT (protein kinase B) in myotubes.

In another exemplary embodiment of the present disclosure, the composition may have an effect of preventing and/or improving reduction of muscle fascicle, infiltration of inflammatory cells into muscle, and local fibrosis.

In another exemplary embodiment of the present disclosure, the muscle atrophy and/or muscle loss may include qualitative loss caused by decreased diameter of myotubes and quantitative loss caused by decreased number of myotubes.

The present disclosure also provides a method for preparing a composition for preventing or improving muscle atrophy, which includes:
(a) a lycii radicis cortex pulverization step of preparing a lycii radicis cortex (*Lycium chinense*) powder by pulverizing dried lycii radicis cortex; and (b) an extraction step of preparing an extract by mixing the pulverized lycii radicis cortex powder with one or more solvent selected from a group consisting of water ($H_2O$), a $C_1$-$C_4$ lower alcohol and a mixture thereof.

In an exemplary embodiment of the present disclosure, the lycii radicis cortex refers to the root bark (rhizodermis) of Chinese matrimony vine, and may include the whole root of Chinese matrimony vine.

In another exemplary embodiment of the present disclosure, the lycii radicis cortex extract may be obtained by mixing one or more part of Chinese matrimony vine selected from root, branch and stem with an extraction solvent.

The present disclosure also provides a method for preventing or treating atrophy, which includes a step of administering the lycii radicis cortex extract to an individual.

The present disclosure also provides a use of the lycii radicis cortex extract for preparing a medicine for preventing or treating atrophy.

In an exemplary embodiment of the present disclosure, the muscle atrophy may be one or more selected from a group consisting of sarcopenia, disuse atrophy, mechanical unloading-induced atrophy, denervation atrophy, cachexia, drug-induced atrophy, malnutritional atrophy and muscular dystrophy.

Advantageous Effects

A composition for preventing and treating muscle atrophy, containing a lycii radicis cortex extract as an active ingredient, of the present disclosure inhibits proteins that may act as muscle fiber atrophy factors and increase the activity of proteins involved in myoprotein synthesis and, thus, can be usefully used for preventing and treating muscle atrophy.

Figure 7A:
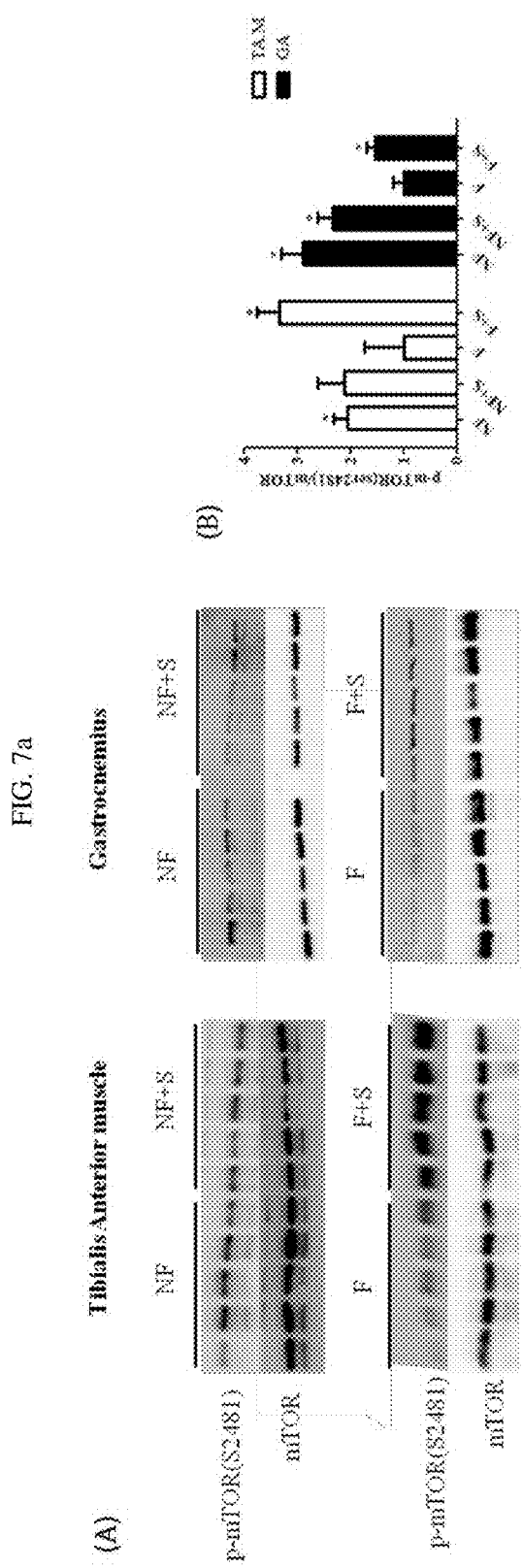
Figure 7B:
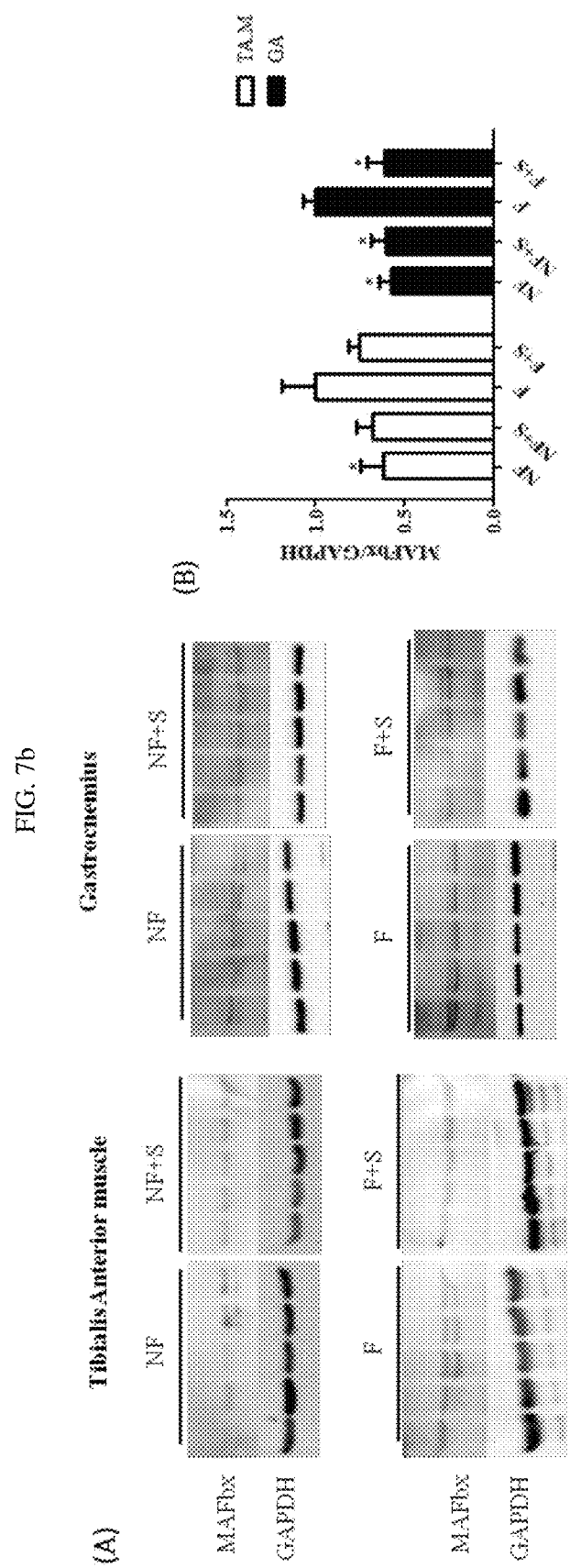
Figure 7C:
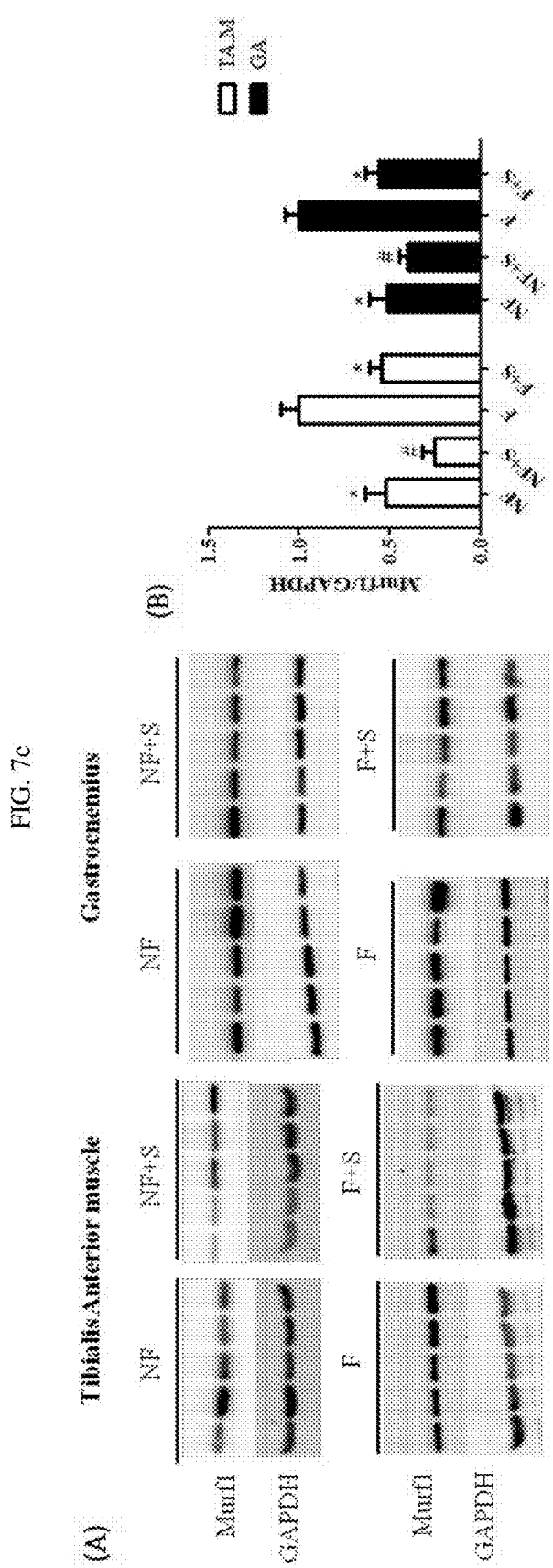
Figure 7D:
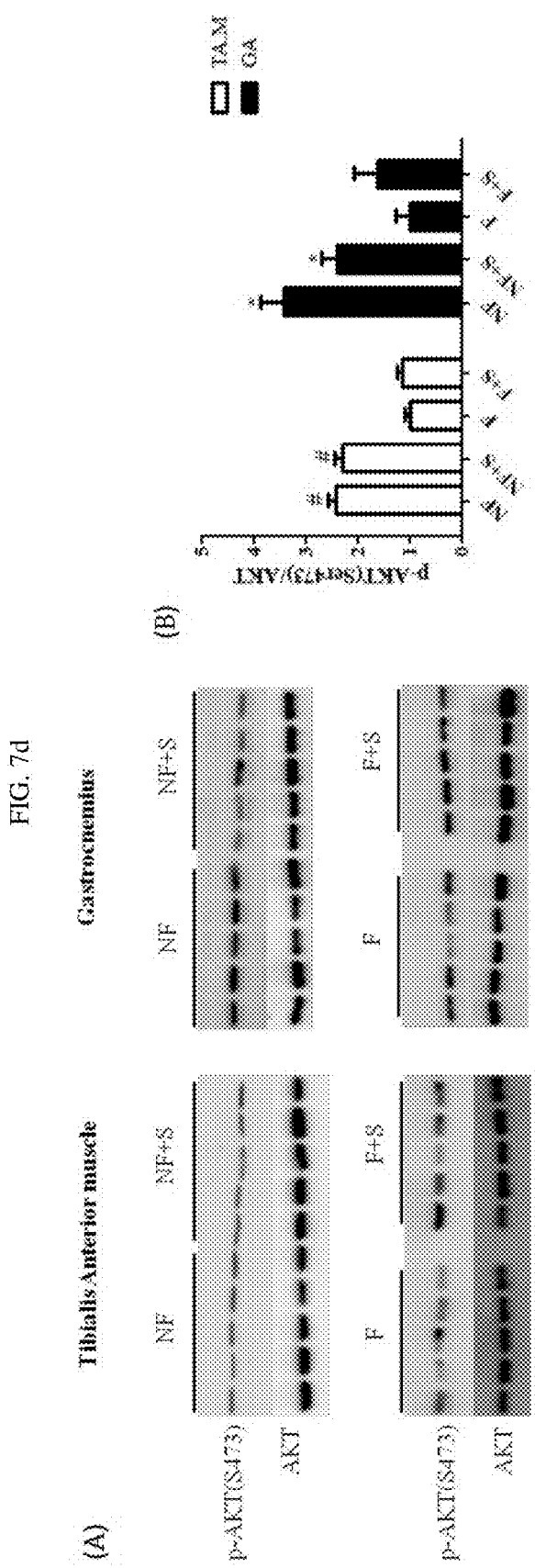

(A) of FIG. 7a through (B) of FIG. 7d show a result of investigating the muscle atrophy mechanism (AKT/mTOR mechanism) and the change in the expression level of atrogin-1/MAFbx and MuRF-1 depending on the administration of a lycii radicis cortex extract to a fasting animal model

BEST MODE

The inventors of the present disclosure have researched to explore naturally derived ingredients capable of alleviating skeletal muscle loss. As a result, they have identified that the decrease of the diameter of C2C12 cells caused by dexamethasone can be effectively prevented by treating with a lycii radicis cortex extract and that muscle loss can be reduced remarkably in a fasting-induced muscle loss animal model by administering a lycii radicis cortex extract, and have completed the present disclosure.

Therefore, the present disclosure is directed to providing a use of a lycii radicis cortex (*Lycium chinense*) extract for preventing, improving and/or treating muscle atrophy. The lycii radicis cortex extract of the present disclosure may be extracted according to conventional methods of extracting from natural products known in the art, i.e., under conventional temperature and pressure conditions using common solvents. For example, in the present disclosure, the lycii radicis cortex extract may be extracted using one or more solvent selected from a group consisting of water, a $C_1$-$C_4$ alcohol, n-hexane, ethyl acetate, acetone, butyl acetate, 1,3-butylene glycol, methylene chloride and a mixture thereof, specifically using a mixture solvent of water and a $C_1$-$C_4$ alcohol at a volume ratio of 1:5 to 1:1, more specifically using 50% ethanol. The extraction efficiency of the ingredients of the lycii radicis cortex effective in improvising muscle atrophy may vary depending on the mixing ratio.

The extract may be extracted from the lycii radicis cortex by various methods such as hot water extraction, cold immersion extraction, reflux extraction, ultrasonic extraction, etc., although not being limited thereto. Specifically, the reflux extraction method may be used.

The prepared extract may be filtered, concentrated or dried to remove the solvent, and may be subjected to all of filtration, concentration and drying. The filtration, concentration or drying may be performed several times. For example, the filtration may be performed using a filter paper or a vacuum filter, the concentration may be performed using a vacuum concentrator, and the drying may be performed by spray drying, freeze drying, etc., although not being limited thereto.

The extract extracted with the solvent may be further subjected to fractionation using a solvent selected from a group consisting of butanol, n-hexane, methylene chloride, acetone, ethyl acetate, ethyl ether, chloroform, water and a mixture thereof, although not being limited thereto.

Also, in the present disclosure, the lycii radicis cortex extract may be extracted by adding an edible acid to the solvent. Specifically, one or more acid selected from a group consisting of acetic acid, citric acid, malic acid, succinic acid, fumaric acid, tartaric acid, an amino acid and lactic acid may be added to the solvent. More specifically, acetic acid may be added and, the acetic acid may be added to the solvent in an amount of 0.1-1 wt %, specifically 0.5 wt %.

The present disclosure provides a method for preparing a lycii radicis cortex extract for improving, preventing or treating muscle atrophy, which includes: (a) a step of preparing a lycii radicis cortex powder by pulverizing dried lycii radicis cortex; and (b) a step of preparing an extract by mixing the pulverized lycii radicis cortex powder with one or more solvent selected from a group consisting of water ($H_2O$), a $C_1$-$C_4$ lower alcohol and a mixture thereof.

The extraction for preparing the extract may be performed by reflux extraction, and the extracted extract may be further subjected to concentration under reduced pressure and freeze drying.

In the present disclosure, the muscle atrophy to be improved, prevented or treated includes sarcopenia, disuse atrophy, mechanical unloading-induced atrophy, denervation atrophy, cachexia, drug-induced atrophy, malnutritional atrophy, muscular dystrophy, etc.

As one example of the muscle atrophy, disuse atrophy (disuse atrophy of muscles) may be caused by casting, etc. that make muscle use impossible. The lycii radicis cortex extract may be used to prevent muscle atrophy that may be caused by such reasons.

The disuse atrophy (disuse atrophy of muscles) includes the decrease of muscle thickness due to limited activity, prolonged bed rest, casting, etc. caused by aging, diseases, etc. The lycii radicis cortex extract may be used to prevent muscle atrophy that may be caused by these causes.

The disuse atrophy is accompanied by various clinical diseases such as peripheral nerve injury, cancer, sepsis, etc. as well as prolonged bed rest, limb casting, aging, etc. In general, muscle atrophy is accompanied by physiological, histochemical and biochemical changes caused by reduced myoproteins and may cause functional disorder of skeletal muscle.

The muscle atrophy may be caused by mechanical unloading and denervation of skeletal muscle. The lycii radicis cortex extract may be used to help prevention and improvement of muscle atrophy that may be caused by such causes.

In denervated muscle cells, quantitative decrease and functional disorder of mitochondria occur and ROS production in mitochondria is increased, leading to increased apoptosis of muscle cells due to oxidative damages.

One of the symptoms of cachexia, a general weakness syndrome that can be found in the late stage of cancer, tuberculosis, hemophilia, etc., is rapid emaciation. The lycii radicis cortex extract may be used to help prevention and improvement of muscle atrophy that may be caused by such causes.

Muscular dystrophy is a disease the main symptoms of which are muscle atrophy and weakened muscular power caused by failure to form the dystrophin-glycoprotein complex constituting the sarcolemma due to genetic mutation. The lycii radicis cortex extract may be used to help prevention and improvement of muscle atrophy that may be caused by such causes.

Cortisol is a substance that can be secreted in the body due to various acute stresses. It supplies energy to cope with stress, but also induces muscle atrophy during its mechanism of action. The lycii radicis cortex extract may be used to help prevention and improvement of muscle atrophy that may be caused by cortisol.

Synthetic adrenocortical hormone agents may cause steroid-induced myopathy, muscle injury, etc. as side effects. The lycii radicis cortex extract may be used to help prevention and improvement of such steroid-induced muscle atrophy.

It was confirmed from experiments that the administration of the lycii radicis cortex extract results in decreased expression of atrogin-1/MAFbx and MuRF-1 in muscle cells. Therefore, the composition of the present disclosure may have an effect of preventing, treating or improving muscle atrophy resulting from reduction of muscle fascicle, infiltration of inflammatory cells into muscle, and local fibrosis.

The pharmaceutical composition of the present disclosure may further contain an adequate carrier, excipient or diluent commonly used to prepare pharmaceutical compositions.

In addition, the pharmaceutical composition of the present disclosure may be formulated into a powder, a granule, a tablet, a capsule, a suspension, an emulsion, a syrup, an aerosol, a formulation for external application, a sterile injection solution, etc. according to common methods. Specifically, it may be formulated into a cream, a gel, a patch, a spray, an ointment, a plaster, a lotion, a liniment, a paste or a cataplasma. The carrier, excipient or diluent that may be contained in the composition containing the lycii radicis cortex extract may be lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate or mineral oil. In general, the formulation is prepared using a commonly used diluent or excipient such as a filler, an extender, a binder, a wetting agent, a disintegrant, a surfactant, etc. Solid formulations for oral administration include a tablet, a pill, a powder, a granule, a capsule, etc. The solid formulation is prepared by mixing the extract with at least one excipient, e.g., starch, calcium carbonate, sucrose, lactose, gelatin, etc. In addition to a simple excipient, a lubricant such as magnesium stearate and talc is also used. Liquid formulations for oral administration include a suspension, a liquid for internal use, an emulsion, a syrup, etc., and may contain various excipients, e.g., a wetting agent, a sweetener, an aromatic, a preservative, etc., in addition to a commonly used simple diluent such as water and liquid paraffin. Formulations for parenteral administration include a sterile aqueous solution, a non-aqueous solution, a suspension, an emulsion, a lyophilized formulation and a suppository. The non-aqueous solution or the suspension may use propylene glycol, polyethylene glycol, vegetable oil such as olive oil, an injectable ester such as ethyl oleate, etc. As a base of the suppository, Witepsol, macrogol, Tween 61, cacao butter, laurin butter, glycerogelatin, etc. may be used.

The specific administration dosage of the pharmaceutical composition of the present disclosure may be selected adequately by those skilled in the art although it varies depending on the physical condition and body weight of a patient, the severity of a disease, drug type, administration route and administration period. In order to achieve a desired effect, the pharmaceutical composition of the present disclosure may be administered at a daily dosage of 0.0001-100 mg/kg, specifically 0.001-10 mg/kg. The administration may be made once or several times a day. However, the administration dosage does not limit the scope of the present disclosure by any means.

The present disclosure provides a method for preventing and/or treating muscle atrophy, which includes a step of administering the lycii radicis cortex extract to an individual.

In the present disclosure the "individual" may be any organism having fibrous muscle tissues without limitation. The organism includes mammals such as rat, mouse, livestock, human, etc., birds, etc. Specifically, the individual may be human and all modes of administration may be expected. For example, the administration may be made orally, rectally, or via intravenous, intramuscular or subcutaneous injection.

The formulation for oral administration may be administered at a daily dosage of 0.1-100 mg/kg, once or several times a day, although the dosage may vary depending on the age, sex and body weight of a patient. In addition, the administration dosage may be increased or decreased depending on the administration route, the severity of a disease, etc. Therefore, the administration dosage does not limit the scope of the present disclosure by any means.

In addition, the present disclosure provides a food composition for improving muscle atrophy and/or muscle loss, which contains a lycii radicis cortex extract as an active ingredient. In addition, the lycii radicis cortex extract may be added to food for the purpose of preventing or delaying muscle atrophy and/or muscle loss, and the food composition of the present disclosure may be used for preparation of functional food, health functional food, etc. When the lycii radicis cortex extract of the present disclosure is used as a food additive, the lycii radicis cortex extract may be adequately used either alone or together with other foods or food ingredients, according to common methods. The mixing amount of the active ingredient may be determined adequately depending on the purpose of use (prevention, health improvement, or therapeutic treatment). In general, when preparing a food or a drink, the lycii radicis cortex extract is added in an amount of 15 wt % or less, specifically 10 wt % or less. However, in case of long-term ingestion for health or hygiene purposes, the amount may be smaller. In addition, the amount of the active ingredient may be larger than the above-described range since it has no problem in terms of safety.

The food is not specially limited. Examples of the food to which the lycii radicis cortex can be added include all types of common food, including meat, sausage, bread, chocolate, candy, snack, confectionery, pizza, ramen, noodle, gum, dairy products including ice cream, soup, beverage, tea, drink, alcoholic beverage, vitamin complex, etc.

A health drink composition according to the present disclosure may further contain various flavors, natural carbohydrates, etc. commonly used in drinks. The natural carbohydrate may be a monosaccharide such as glucose and fructose, a disaccharide such as maltose and sucrose, a polysaccharide such as dextrin and cyclodextrin, or a sugar alcohol such as xylitol, sorbitol, erythritol, etc. As the sweetener, a natural sweetener such as thaumatin and *stevia* extract, a synthetic sweetener such as saccharin and aspartame, etc. may be used. The content of the natural carbohydrate may be generally about 0.01-0.20 g, specifically about 0.04-0.10 g, per 100 mL of the composition of the present disclosure.

In addition, the composition of the present disclosure may contain various nutrients, vitamins, electrolytes, flavors, colorants, pectic acid and its salts, alginic acid and its salts, organic acids, protective colloidal thickeners, pH control agents, stabilizers, antiseptics, glycerin, alcohols, carbonating agents used in carbonated drinks, etc. In addition, the composition of the present disclosure may contain a pulp for preparing natural fruit juice, fruit juice drinks and vegetable drinks. These ingredients may be used either independently or in combination. The content of these additives is of no great importance. In general, the content may be selected in a range of 0.01-0.20 parts by weight based on 100 parts by weight of the composition of the present disclosure.

The term "prevention" used in the present disclosure means any action of preventing or delaying the onset of muscle atrophy or muscle loss by administering the pharmaceutical composition according to the present disclosure.

The term "treatment" used in the present disclosure means any action of improving or alleviating the symptoms of muscle atrophy by administering the pharmaceutical composition according to the present disclosure.

The term "improvement" used in the present disclosure means any action of reducing parameters associated with muscle atrophy or muscle loss, e.g., the degree of symptoms, by administering the pharmaceutical composition according to the present disclosure.

The term "a subject" used in the present disclosure means person who needs to be treated or beware of muscle atrophy or muscle loss.

In the present disclosure, the muscle loss includes quantitative loss caused by decreased number of myotubes and qualitative loss caused by decreased diameter of myotubes.

Lycii radicis cortex refers to the root bark of Chinese matrimony vine (*Lycium chinense* Miller) or Chinese wolfberry (*Lycium barbarum* L) in the family Solanaceae. However, in the present disclosure, the lycii radicis cortex may include, in addition to the root bark of Chinese matrimony vine, the whole root of Chinese matrimony vine. The lycii radicis cortex may be one or more selected from a group consisting of the leaf, branch and stem of Chinese matrimony vine. Specifically, the lycii radicis cortex may be the root bark (rhizodermis) of Chinese matrimony vine. However, since the ingredients of the lycii radicis cortex that prevent or improve muscle atrophy are contained in the whole root of Chinese matrimony vine, the whole root of Chinese matrimony vine including the root bark is also included in the scope of the present disclosure.

Figure 4:
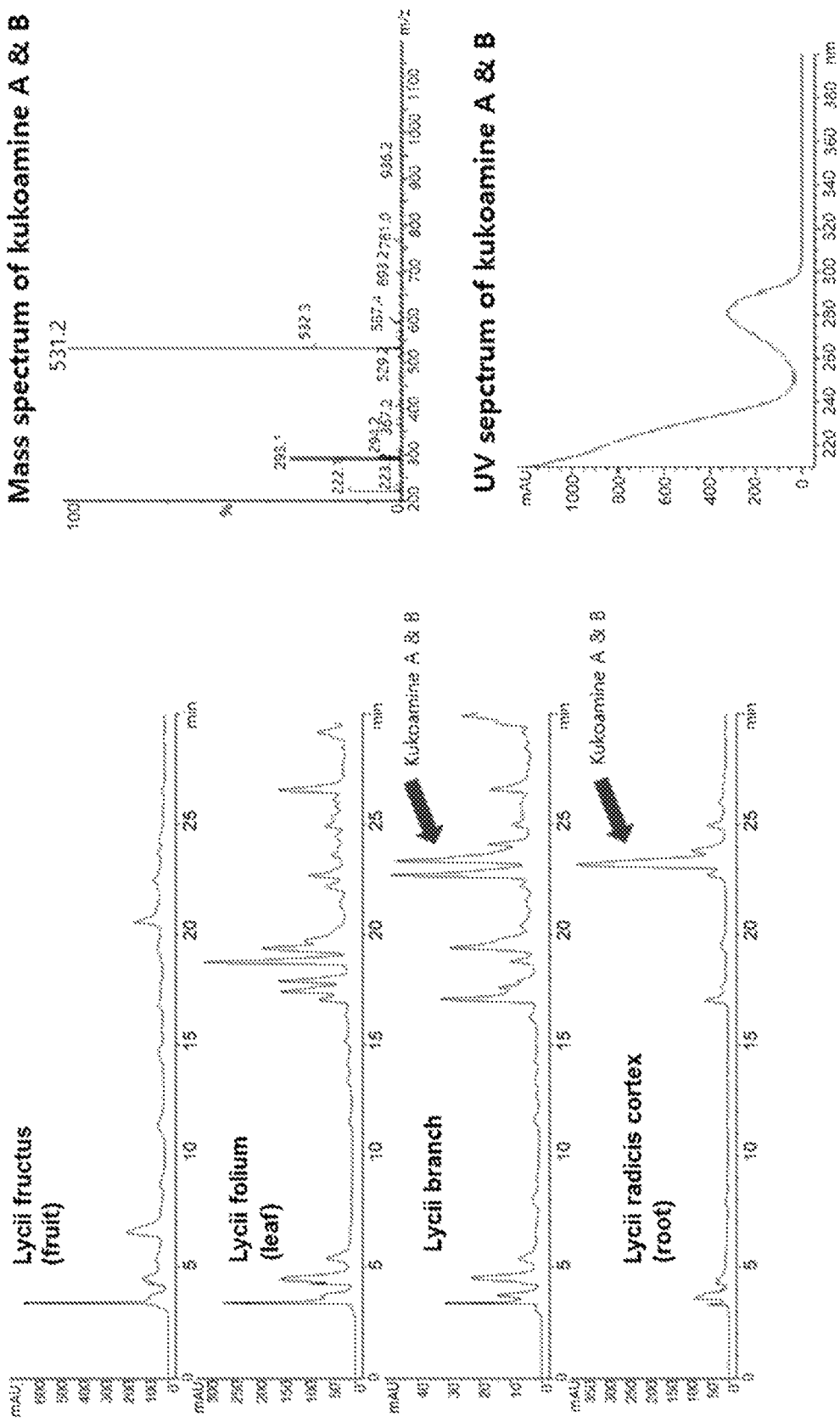
FIG. 4 shows a result of investigating the presence of functional ingredients in different parts of Chinese matrimony vine through HPLC.

In the present disclosure, it was found out that kukoamine A and kukoamine B, which are active ingredients of the lycii radicis cortex (*Lycium chinense*), are included also in the branch of Chinese matrimony vine (FIG. 4).

Hereinafter, the present disclosure will be described in detail through examples. However, the following examples are for illustrative purposes only and it will be apparent to those of ordinary skill in the art that the scope of the present disclosure is not limited by the examples.

Example 1. Preparation of Lycii Radicis Cortex Extract

Korean or Chinese lycii radicis cortex, the root bark of Chinese matrimony vine, was pulverized to an average particle diameter of 0.30-0.50 mm and extracted for 1-4 hours using a 50:50 mixture solvent of ethanol and water. The extract was concentrated using a rotary vacuum evaporator N-N series and then freeze-dried using Heto Power Dry LL3000.

156 g of the extract was obtained from 3 kg of the lycii radicis cortex.

Example 2. Confirmation of Effect of Preventing and Improving Muscle Atrophy of Lycii Radicis Cortex Extract In Vitro 2-1. Culturing of C2C12 Cells and Induction of Differentiation C2C12 mouse myoblasts acquired from the Korean Collection for Type Cultures of the Korea Research Institute of Bioscience and Biotechnology were induced to divide for a total of 6 times (3 times×2 days). After the division was completed sufficiently, the C2C12 cells were seeded onto a 12-well plate and then divided for 2 days. As a division medium, HyClone™ DMEM/high glucose supplemented with 10% FBS (fetal bovine serum) and 1% penicillin was used.

When each well of the 12-well plate reached 90% confluency, the cells were treated with a differentiation medium (HyClone™ DMEM/high glucose supplemented with 2% HS (horse serum) and 1% penicillin). The differentiation medium was replaced every 2 days, and the treatment was performed for 6 days. Then, the differentiation-induced C2C12 myotubes were treated with HyClone™ supplemented with 1% penicillin for 24 hours and then subjected to the following experiment.

2-2. Induction of Muscle Atrophy with Dexamethasone and Treatment with Lycii Radicis Cortex Extract Dexamethasone induces muscle atrophy by inhibiting muscle synthesis and inducing protein degradation. The effect of preventing and improving muscle atrophy of the lycii radicis cortex extract was investigated by inducing muscle atrophy by treating the differentiation-induced C2C12 cells of Example 2-1 with dexamethasone and then treating the muscle atrophy-induced cells with the lycii radicis cortex extract. Detailed experimental conditions are as follows.

(1) Control: The differentiated C2C12 cells were treated only with DMEM/high glucose supplemented with 1% penicillin for 48 hours.

(2) Negative control: The C2C12 cells were treated with DMEM/high glucose supplemented with 1% penicillin and 1 µM dexamethasone for 48 hours.

(3) Control+lycii radicis cortex extract: The cells were treated with 30 µg/mL of the lycii radicis cortex extract for 48 hours under the same condition as the control of (1).

(4) Negative control+lycii radicis cortex extract: The cells were treated with 30 µg/mL of the lycii radicis cortex extract for 48 hours under the same condition as the negative control of (2).

2-3. Measurement of Diameter of C2C12 Myotubes

After treating the control groups and test groups for 48 hours in Example 2-2, the cells were imaged using the automated cell imaging system JuLi™ Stage and the thickness of the imaged cells was measured using the cell processing program Image J, with 50 cells per group. Average and standard error are summarized in Table 1.

TABLE 1

|  | Control | Dex | Lycii radicis cortex | Dex + lycii radicis cortex |
|---|---|---|---|---|
| Average thickness (μm) of 50 cells | 10.9318 | 7.5933 | 11.0932 | 8.9169 |
| Standard error (μm) of 50 cells | 3.1504 | 2.6694 | 3.5770 | 2.1480 |
| Standard error (μm) of 50 cells | 0.4384 | 0.3714 | 0.6388 | 0.2990 |

(Dex: dexamethasone (1 μM), lycii radicis cortex: concentration of lycii radicis cortex extract: 30 μg/mL)

Figure 1:
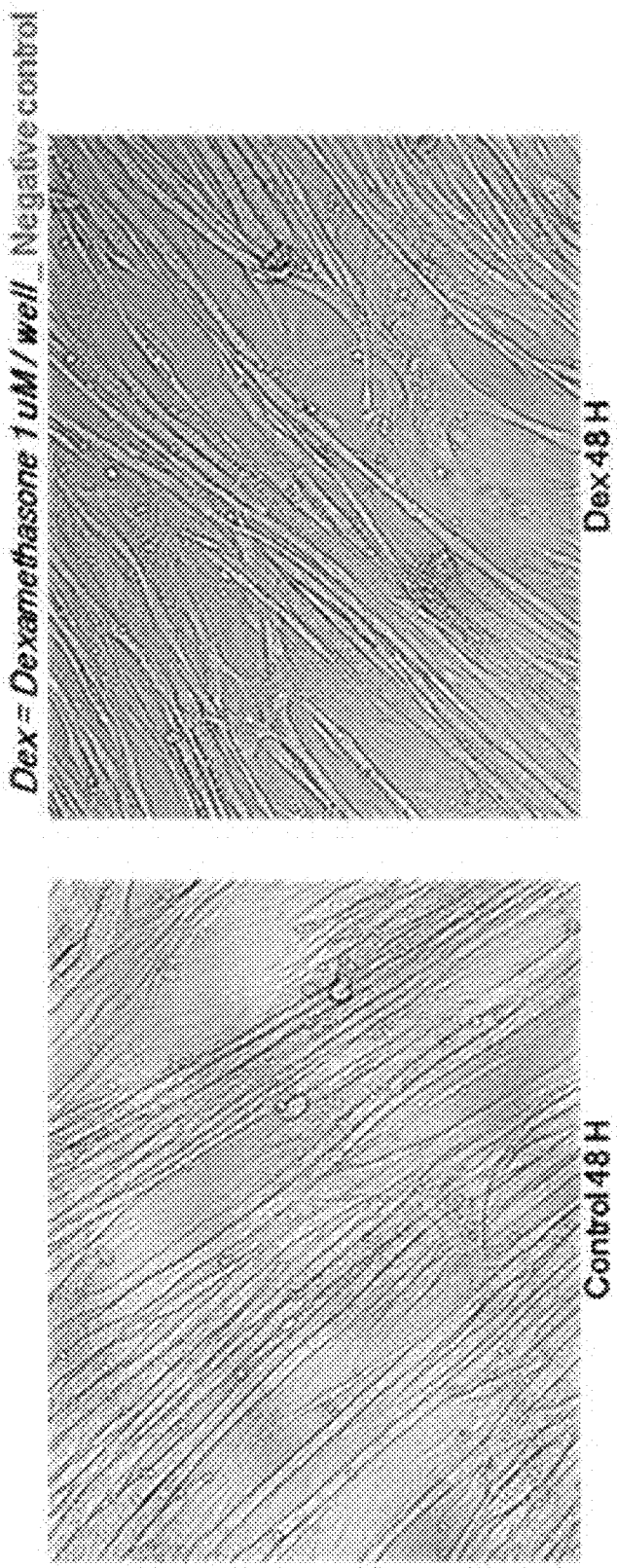
FIG. 1 shows a result of comparing the thickness of C2C12 myotubes depending on treatment with dexamethasone.
Figure 2:
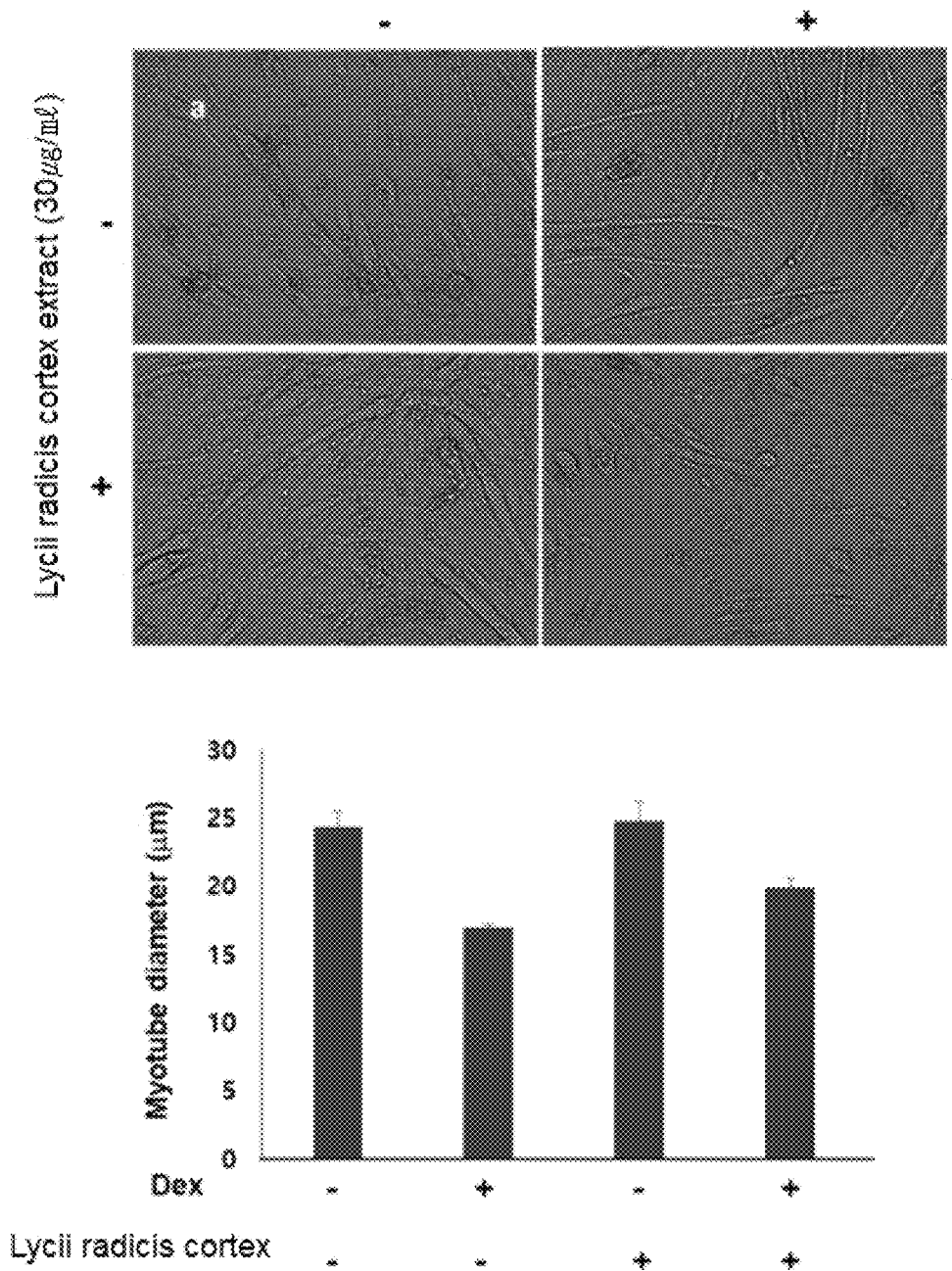
FIG. 2 shows a result of comparing the thickness of C2C12 myotubes treated with a control substance, dexamethasone, a lycii radicis cortex extract, and dexamethasone+ lycii radicis cortex extract.

As a result, it was confirmed that the treatment with dexamethasone results in decreased thickness of C2C12 myotubes (FIG. 1) and that the treatment with the lycii radicis cortex extract provides an improving effect (Table 1 and FIG. 2).

Detailed experimental result is as follows.

(1) The group administered with 'nutrient medium+dexamethasone 1 μM' showed 30.54% decrease in thickness as compared to the control group administered with the basal nutrient medium. This difference was statistically very significant ($p<0.005$).

(2) The group administered with 'nutrient medium+lycii radicis cortex 30 μg/mL' showed about 1.4% increase in thickness as compared to the control group administered with the basal nutrient medium, which was statistically insignificant.

(3) The group administered with 'nutrient medium+dexamethasone 1 μM+lycii radicis cortex 30 μg/mL' showed about 17.4% increase in thickness as compared to the negative control group administered with 'nutrient medium+dexamethasone 1 μM', which was statistically very significant ($p<0.005$).

(4) The recovery rate ('Dex+lycii radicis cortex'-Dex as compared to Control-Dex) was calculated as 39.6%, meaning that the rate of damage recovery by the lycii radicis cortex was 39.6%.

Accordingly, it was confirmed that the lycii radicis cortex exhibits very high recovery rate of muscle atrophy as compared to dexamethasone.

2-4. Confirmation of Expression Level of Muscle Atrophy-Related Proteins

For the control and test groups treated under the four conditions in Example 2-2, the biological activity of the lycii radicis cortex extract was investigated by measuring the expression level and activity of atrogin-1/MAFbx and MuRF-1, involved in the muscle atrophy-inducing pathway, by western blotting.

Figure 3:
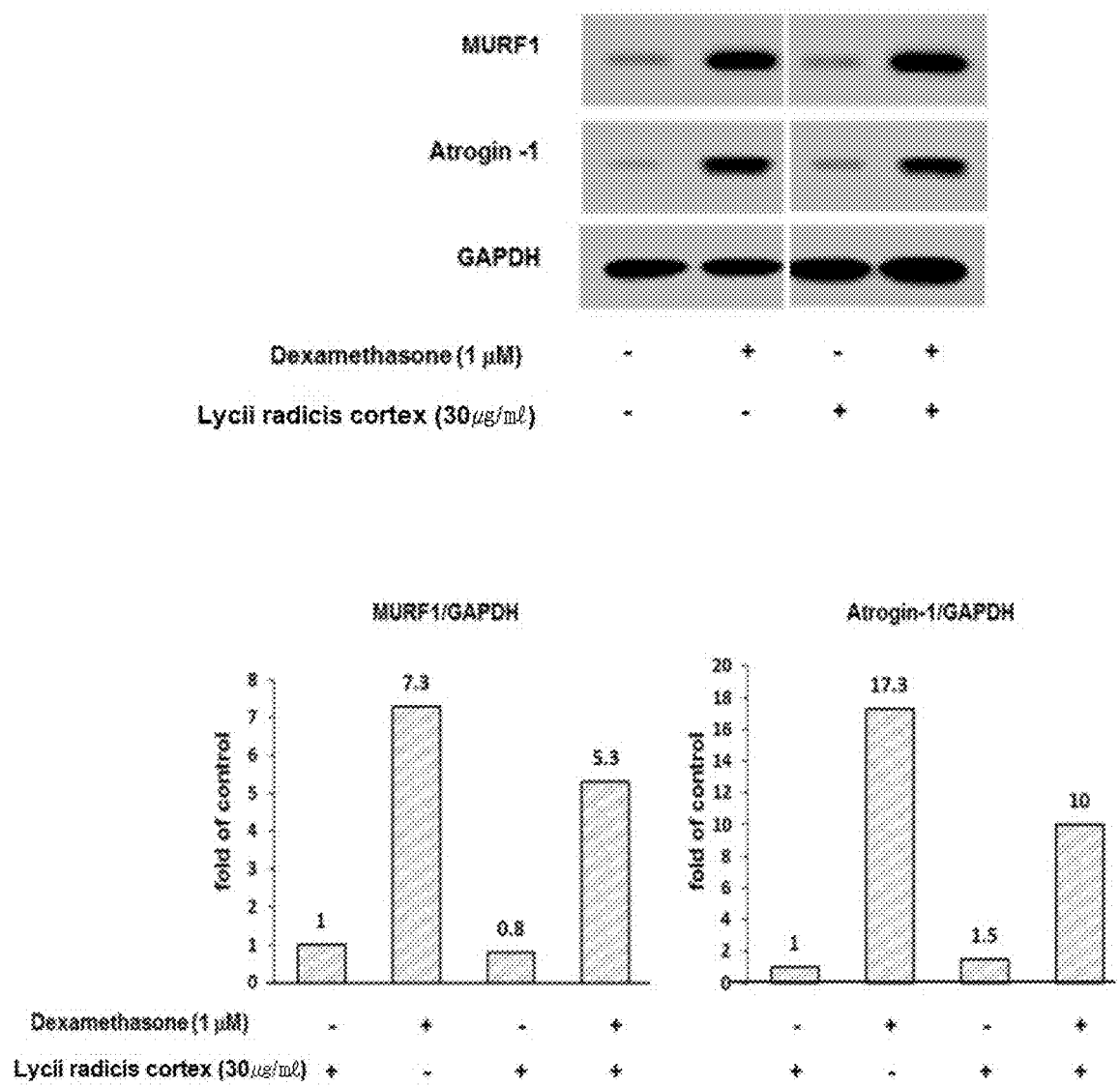
FIG. 3 shows a western blotting result and result of investigating the activity of MuRF-1 and atrogin-1/MAFbx for C2C12 myotubes.

As a result, it was confirmed that the treatment of the C2C12 myotubes with dexamethasone increases atrogin-1/MAFbx and MuRF-1, and the treatment with the lycii radicis cortex extract decreases the two proteins (Table 2 and FIG. 3).

Table 2 shows a result of comparing the activity of atrogin-1/MAFbx and MuRF-1 depending on the treatment.

TABLE 2

|  | Control | Dex | Lycii radicis cortex | Dex + lycii radicis cortex |
|---|---|---|---|---|
| Atrogin-1/MAFbx vs. GAPDH | 100 | 340.3945 | 82.6257 | 264.106 |
| MuRF-1 vs. GAPDH | 100 | 351.2904 | 93.5111 | 233.8061 |

The result of investigating the activity of the atrogin-1/MAFbx and MuRF-1 proteins under the four conditions is as follows.

(1) It was confirmed that the activity of atrogin-1/MAFbx and MuRF-1 was increased 3.404-fold and 3.513-fold, respectively, in the group administered with 'nutrient medium+dexamethasone 1 μM' as compared to the control group administered with the basal nutrient medium.

(2) It was confirmed that the activity of atrogin-1/MAFbx and MuRF-1 was decreased by 18.38% and 6.5%, respectively, in the group administered with 'nutrient medium+lycii radicis cortex 30 μg/mL' as compared to the control group administered with the basal nutrient medium.

(3) It was confirmed that the activity of atrogin-1/MAFbx and MuRF-1 was decreased by 22.5% and 33.5%, respectively, in the group administered with 'nutrient medium+dexamethasone 1 μM+lycii radicis cortex 30 μg/mL' as compared to the negative control group administered with 'nutrient medium+dexamethasone 1 μM'.

(4) The recovery rate ('Dex+lycii radicis cortex'-Dex as compared to Control-Dex) was calculated as 31.8% and 46.8%, respectively, for atrogin-1/MAFbx and MuRF-1.

Accordingly, it was confirmed that the lycii radicis cortex exhibits very high recovery rate of muscle atrophy as compared to dexamethasone.

In addition, the effect of enhancing muscle synthesis may be expected since the activity of the muscle atrophy-inducing proteins is decreased regardless of dexamethasone.

Example 3. Confirmation of Effect of Preventing and Improving Muscle Atrophy of Lycii Radicis Cortex Extract In Vivo 3-1. Experimental Animals As experimental animals, 11-week-old C57BL/6 mice (male) acquired from Hana Bio (Seongnam, Gyeonggi-do, Korea) were quarantined, adapted and raised for a week in the cages of Dongnam Medicinal Chemistry Research Center (Animal Facility Registration No. 412). During the raising, feed and water were available ad libitum (lights on 07:00-19:00). The experiment was conducted according to the guideline of the Institutional Animal Care and Use Committee (SEMI-19-010) of Dongnam Medicinal Chemistry Research Center.

3-2. Induction of Muscle Loss Model and Sample Administration

Figure 5:
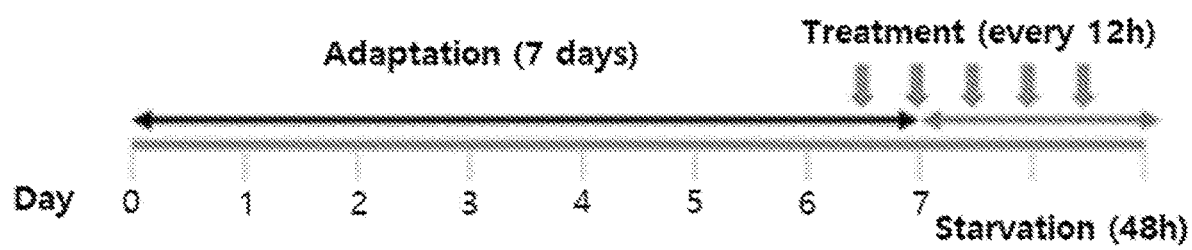
FIG. 5 is a schematic of an animal experiment design for investigating the effect of preventing and improving muscle loss of a lycii radicis cortex extract. It shows a sample administration schedule for a fasting-induced muscle atrophy animal model.
Figure 6A:
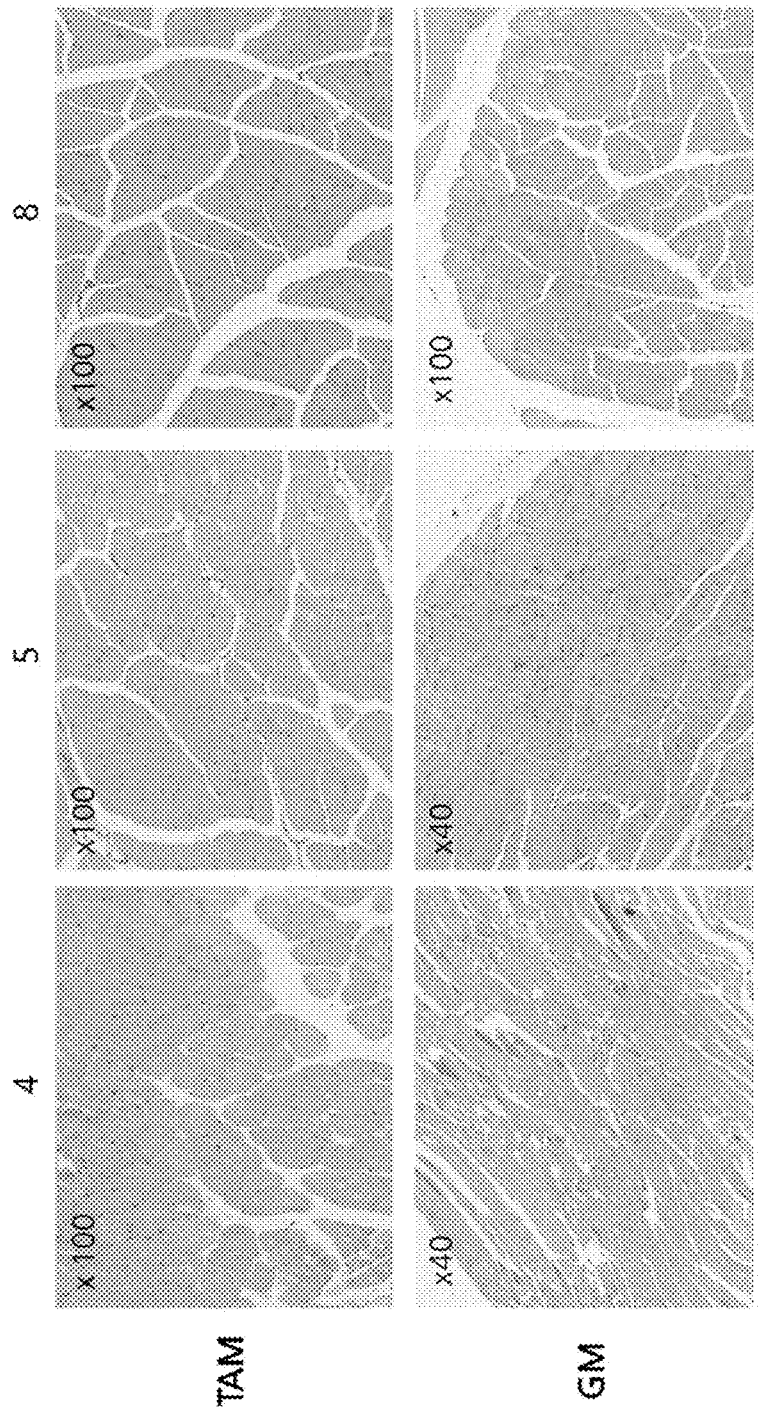
FIGS. 6a-6d show a H&E staining result for tibialis anterior muscle and gastrocnemius muscle tissues after fasting of or administration of a lycii radicis cortex extract to an animal model.
Figure 6B:
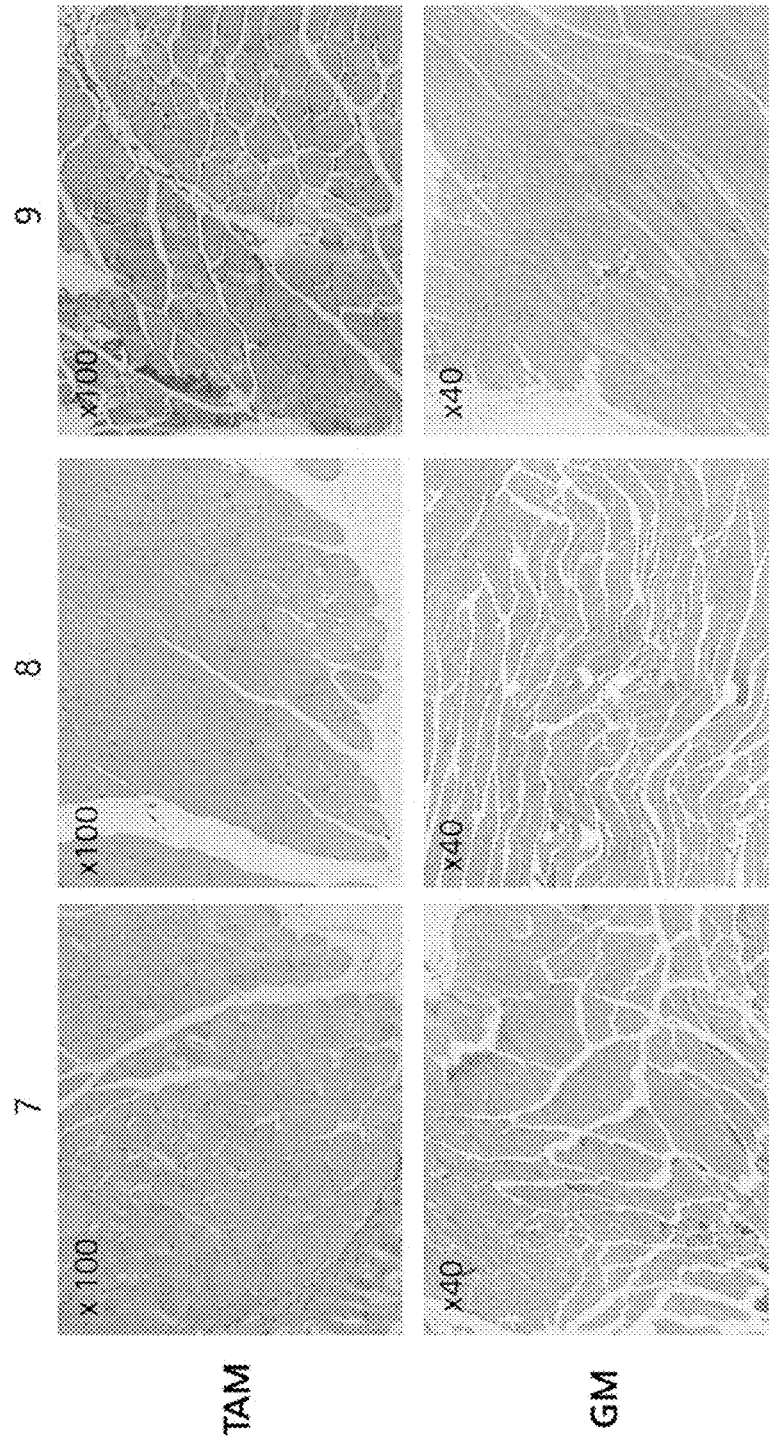
Figure 6C:
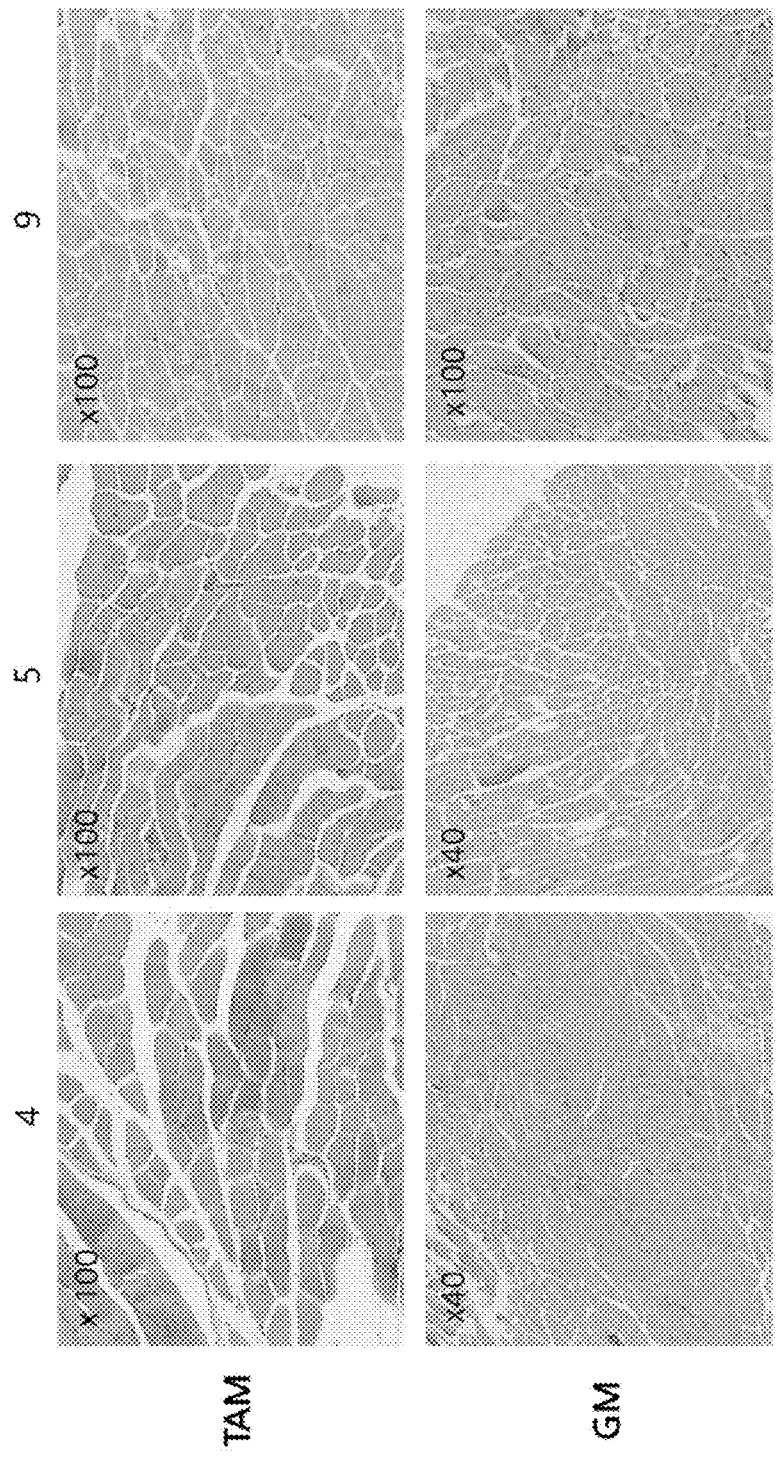
Figure 6D:
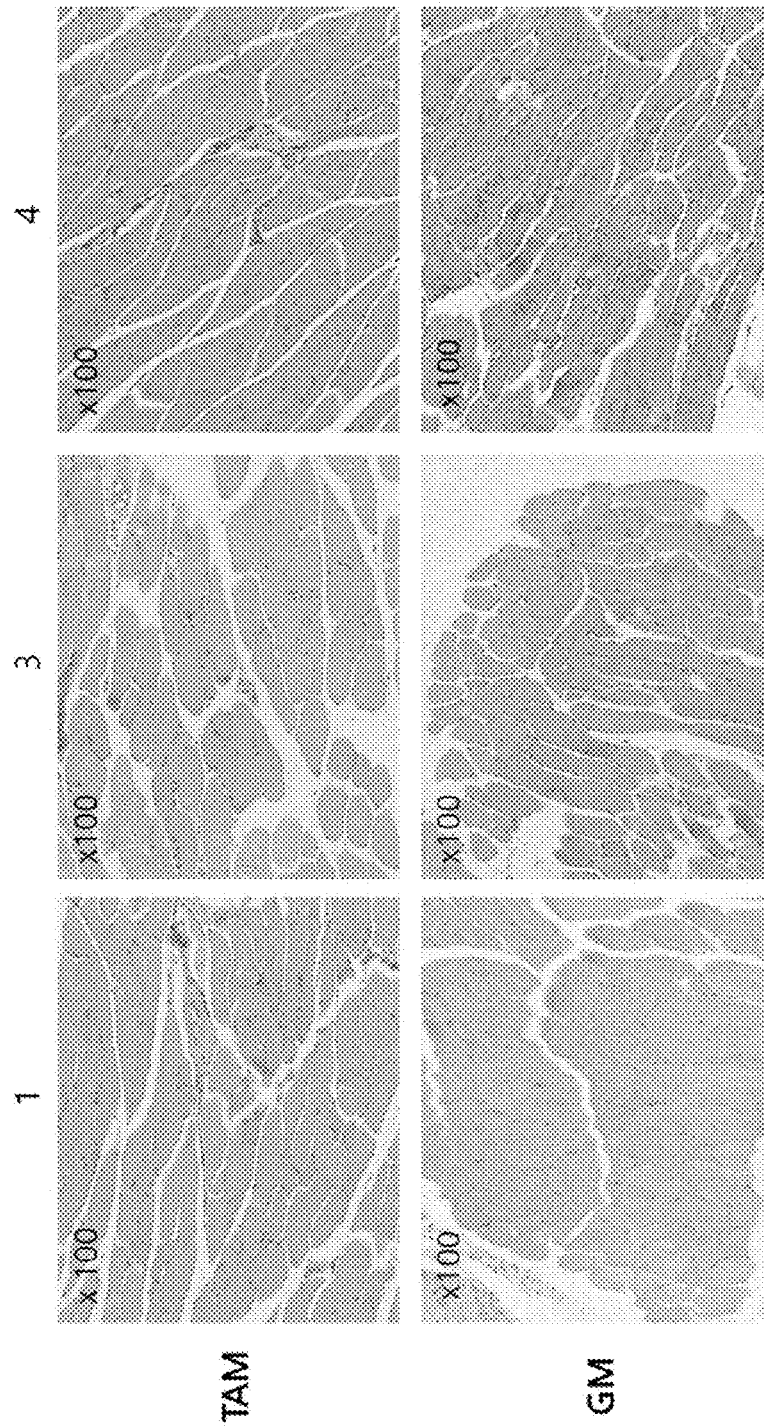

After the adaptation, experiment was conducted as shown in FIG. 5 and as described in Table 3. The experimental animals were treated regularly (10:00-12:00 am) while providing solid feed (Nana Bio, Seongnam, Gyeonggi-do, Korea). Body weight change was measured for a total of 5 times. The animals of fasting groups were raised in different cages during the fasting period. Sample administration was made once at 12 hours before the end of the adaptation, once at the onset of fasting, and 3 times thereafter with 12-hour intervals (5 times in total).

TABLE 3

| Group | Treatment | Dose (mg/kg) | N |
|---|---|---|---|
| NF (non-fasting) | Normal diet (saline) | — | 9 |
| NF + S (non-fasting + sample) | Normal diet + administration of lycii radicis cortex extract | 50 | 9 |

TABLE 3-continued

| Group | Treatment | Dose (mg/kg) | N |
|---|---|---|---|
| F (fasting) | Fasting for 48 hours (saline) | — | 9 |
| F + S (fasting + sample) | Fasting for 48 hours + administration of lycii radicis cortex extract | 50 | 9 |

The experimental result was represented with average and standard deviation, and the significance between the groups was tested by ANOVA t-test using the Statview program.

3-3. Change in Body Weight

Whereas the non-fasting group showed normal body weight change, the fasting group (F) showed significant decrease in body weight after fasting for 48 hours. The F+S group showed slight but insignificant increase in body weight (Table 4).

TABLE 4

| | Body weight (g) | | |
|---|---|---|---|
| Group | Initial | Onset of sample administration | End of sample administration |
| NF | 23.886 ± 0.578 [n.s] | 26.011 ± 1.000 [n.s] | 26.253 ± 0.878 [#] |
| NF + S | 23.869 ± 0.382 | 25.674 ± 0.703 | 26.034 ± 0.910 [#] |
| F | 23.854 ± 0.376 | 25.536 ± 1.173 | 19.526 ± 1.027 |
| F + S | 23.863 ± 0.304 | 25.981 ± 0.525 | 19.980 ± 0.741 |

(n.s: not significant, [#] $p < 0.001$ vs. F)

3-4. Evaluation of Endurance

After the fasting was completed, muscle endurance was evaluated using a treadmill. Running test was conducted until exhaustion. The mice were forced to run at a speed of 12 m/min for 10 minutes, and the mice that could not follow the speed for 10 seconds or longer were regarded as exhausted.

As a result of conducting the running test at a speed of 12 m/min for 10 minutes, the F+S group to which the lycii radicis cortex extract showed a running time of 7.4±3.2 minutes whereas the F group showed a running time of 3.1±1.5 minutes, as shown in Table 5.

TABLE 5

| Group | Treadmill (min) |
|---|---|
| NF | 9.7 ± 0.7 [#] |
| NF + S | 9.7 ± 0.2 [#] |
| F | 3.1 ± 1.5 |
| F + S | 7.4 ± 3.2 [#] |

([#] $p < 0.001$ vs. F)

3-5. Weight of Muscle Tissues (Tibialis Anterior Muscle and Gastrocnemius Muscle)

In order to investigate muscle loss, the weight of tibialis anterior muscle (TA.M) and gastrocnemius muscle (GA) was measured after autopsy (Table 6). The weight of tibialis anterior muscle decreased due to fasting was increased by the administration of the lycii radicis cortex extract (p<0.001), and the same result was observed for gastrocnemius muscle (p<0.05). This result suggests that the decreased muscle mass is restored by the lycii radicis cortex extract as the protein synthesis in muscle is increased.

TABLE 6

| Group | Tibialis Anterior muscle (g) | Gastrocnemius (g) |
|---|---|---|
| NF | 0.106 ± 0.006 [#] | 0.138 ± 0.036 [*] |
| NF + S | 0.099 ± 0.011 [#] | 0.116 ± 0.014 |
| F | 0.055 ± 0.009 | 0.095 ± 0.020 |
| F + S | 0.075 ± 0.009 [#] | 0.129 ± 0.016 [*] |

(* $p < 0.05$ vs. F, [#] $p < 0.001$ vs. F)

3-6. Expression Level of Proteins Related with Muscle Loss and Muscle Hypertrophy mTOR signaling, which induces muscle loss, is related with the expression of mTOR responsible for myoprotein synthesis and atrogin-1/MAFbx and MuRF-1 proteins associated with increase in inflammatory cytokines and inflammation-inducing cytokines due to muscle loss, and selectively decreased expression of AKT. Therefore, the effect of the lycii radicis cortex extract of preventing and improving muscle loss in a fasting-induced muscle loss animal model was investigated biochemically.

Specifically, for protein analysis, 50 mg of muscle tissues (tibialis anterior muscle and gastrocnemius muscle) were added to 300 μL of a RIPA buffer and, after homogenization, centrifuged at 4° C. and 12,000 rpm for 20 minutes. After quantification of proteins by the Bradford assay, the proteins were separated by size by SDS-PAGE (polyacrylamide gel electrophoresis). After transferring the proteins to a PVDF membrane using a semi-dry transfer system (Bio-Rad, USA), the proteins were treated with a blocking buffer containing 5% skim milk for 1 hour. After washing with a 1×TBST buffer for 10 minutes 3 times and then treating with a primary antibody and p-mTOR (ser2481), mTOR, p-AKT (ser473), AKT, MuRF-1, atrogin-1/MAFbx or GAPDH at a ratio of 1:1000, the reaction solution was incubated overnight at 4° C. and washed with a 1×TBST buffer for 10 minutes 3 times. After reaction with a membrane using a western blot detection kit, expression level was measured using ChemiDoc and compared with those of GAPDH, mTOR and AKT.

As a result, the activity of mTOR responsible for myoprotein synthesis, which was decreased due to fasting, was increased significantly in the F+S group administered with the sample (p<0.05) (FIG. 7a).

In addition, the F group, which was fasted for 48 hours, showed increased expression of atrogin-1/MAFbx and MuRF-1, which was consistent with the muscle loss and increased inflammation in muscle due to fasting. Meanwhile, the F+S group, which was administered with the sample, showed significant decrease in the expression of atrogin-1/MAFbx and MuRF-1, suggesting that the muscle loss caused by fasting was reduced (FIG. 7b and FIG. 7c).

In addition, the F group, which was fasted for 48 hours, showed significant decrease of AKT expression in tibialis anterior muscle and gastrocnemius muscle as compared to the NF group administered with normal diet. In contrast, the F+S group showed increased expression of AKT, but there was no significant difference (FIG. 7d).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A method for treating muscle atrophy, comprising:
   administering an effective amount of a composition including a lycii radicis cortex extract as an active ingredient to a subject.

2. The method according to claim 1, wherein the lycii radicis cortex extract is one extracted with one or more solvents selected from the group consisting of water ($H_2O$), a $C_1$-$C_4$ lower alcohol, n-hexane, ethyl acetate, acetone, butyl acetate, 1,3-butylene glycol, methylene chloride and a mixture thereof.

3. The method according to claim 1, wherein the lycii radicis cortex extract is extracted with 50% ethanol as a solvent.

4. The method according to claim 1, wherein the muscle atrophy is one or more selected from the group consisting of sarcopenia, disuse atrophy, mechanical unloading-induced atrophy, denervation atrophy, cachexia, drug-induced atrophy, malnutritional atrophy and muscular dystrophy.

5. The method according to claim 1, wherein the composition decreases the expression of one or more selected from the group consisting of MuRF-1 and atrogin-1/MAFbx in myotubes.

6. The method according to claim 1, wherein the composition increases the expression of one or more selected from the group consisting of mTOR and AKT in myotubes.

* * * * *